(12) United States Patent
Ryu et al.

(10) Patent No.: US 7,923,443 B2
(45) Date of Patent: Apr. 12, 2011

(54) PHARMACEUTICAL COMPOSITION FOR THE TREATMENT OF BONE FRACTURE

(75) Inventors: Jei Man Ryu, Anyang-si (KR); Jin Soo Lee, Yongin-si (KR); Sae Kwang Ku, Suwon-si (KR); Jung Woo Lee, Uiwang-si (KR); Hee Bog Yang, Gunpo-si (KR)

(73) Assignee: Dong Wha Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 11/631,828

(22) PCT Filed: Jul. 5, 2005

(86) PCT No.: PCT/KR2005/002138
§ 371 (c)(1),
(2), (4) Date: Feb. 7, 2008

(87) PCT Pub. No.: WO2006/004369
PCT Pub. Date: Jan. 12, 2006

(65) Prior Publication Data
US 2008/0287509 A1    Nov. 20, 2008

(30) Foreign Application Priority Data
Jul. 5, 2004   (KR) .................. 10-2004-0052069

(51) Int. Cl.
*A01N 43/00* (2006.01)
*A61K 31/33* (2006.01)

(52) U.S. Cl. ....................................... 514/183

(58) Field of Classification Search ............ 514/183
See application file for complete search history.

(56) References Cited

U.S. PATENT DOCUMENTS

2002/0037279 A1 *   3/2002   Vandenburgh .......... 424/93.21

FOREIGN PATENT DOCUMENTS

| WO | WO98/33779 A1 | 8/1998 |
| WO | WO 03007947 A1 * | 1/2003 |

OTHER PUBLICATIONS

Cebesoy, Oguz, et al.; "Effect of strontium ranelate on fracture healing in rat tibia"; Joint Bone Spine, vol. 74 (2007), pp. 590-593, 2007 Elsevier Masson SAS.

Li, Jiliang, et al.; "Effect of Bisphosphonate (Incadronate) on Fracture Healing of Long Bones in Rats"; Journal of Bone and Mineral Research, vol. 14, No. 6 (1999), pp. 969-979, Blackwell Science, Inc., 1999 American Society for Bone and Mineral Research.

Fleisch, Herbert; "Can Bisphosphonates Be Given to Patients with Fractures?"; Journal of Bone and Mineral Research, vol. 16, No. 3 (2001), pp. 437-440, 2001 American Society for Bone and Mineral Research.

Kinoshita, T., et al.; "Phosphodiesterase Inhibitors, Pentoxifylline and Rolipram, Increase Bone Mass Mainly by Promoting Bone Formation in Normal Mice"; Bone, vol. 27, No. 6, pp. 811-817, Dec. 2000, 2000 Elsevier Science Inc.

Wang Elizabeth A., et al.; "Recombinant human bone morphogenetic protein induces bone formation"; Proc. Natl. Acad. Sci. USA, vol. 87, pp. 2220-2224, Mar. 1990.

Kawamura, Morio, M.D., et al.; "Induction of Callus Formation by Implants of Bone Morphogenetic Protein and Associated Bone Matrix Noncollagenous Proteins"; Clinical Orthopaedics & Related Research, vol. 236, pp. 240-248, Nov. 1998.

Li, Chaoyang, et al.; "Long-Term Effect of Incadronate Disodium (YM-175) on Fracture Healing of Femoral Shaft in Growing Rats"; Journal of Bone and Mineral Research, vol. 16, No. 3, pp. 429-436, 2001, 2001 American Society for Bone and Mineral Research.

Traumatol, Chin J. et al.; "Early period of fracture healing in ovariectomized rats"; Abstract (1 pg.); PubMed (www.pubmed.gov), vol. 6, No. 3, pp. 160-166, Jun. 2003, PMID: 12749788 [PUBMED—indexed for MEDLINE].

Lee, Sung-Eun, "Design, Syntheses, and Evaluation of Functional Molecules for the Treatment of LTB4 Related Disease and Electroluminescent Device"; Aug. 1999.

* cited by examiner

*Primary Examiner* — Brandon J Fetterolf
*Assistant Examiner* — Jean Cornet
(74) *Attorney, Agent, or Firm* — Arent Fox LLP

(57) ABSTRACT

Disclosed herein is a composition for the treatment bone fracture comprising N-hydroxy-4-{5-[4-( 5-isopropyl-2-methyl-1,3-thiazol-4-yl)phenoxy]pentoxyl-benzamidine, 4-{5-[4-(5-isopropyl-2-methyl-1,3-thiazol-4-yl) phenoxy]pentoxy}-benzamidine or pharmaceutically acceptable salts thereof as a medicinally effective ingredient. The composition of the present invention can significantly reduce the volume of bony callus, and increase bony density and strength of bony callus, and decrease the contents of connective tissue and cartilage tissue in bony callus, and thus promote loss and ossification of the bony callus formed during the fracture healing process. Therefore, the composition of the present invention is useful for the treatment of bone fracture.

12 Claims, 1 Drawing Sheet

1. 7 days after fracture induction and drug administration 2. 14 days after fracture induction and drug administration 3. 21 days after fracture induction and drug administration 4. 28 days after fracture induction and drug administration a. Control group
b. Group administrated with the compound of Formula 1 (10 mg/kg)
c. Group administrated with the compound of Formula 1 (50 mg/kg)

PHARMACEUTICAL COMPOSITION FOR THE TREATMENT OF BONE FRACTURE

TECHNICAL FIELD

The present invention relates, in general, to a pharmaceutical composition for the treatment of bone fractures and, more particularly, to a pharmaceutical composition comprising N-hydroxy-4-{5-[4-(5-isopropyl-2-methyl-1,3-thiazol-4-yl)phenoxy]pentoxy}-benzamidine, 4-{5-[4-(5-isopropyl-2-methyl-1,3-thiazol-4-yl)phenoxy]pentoxy}-benzamidine or pharmaceutically acceptable salts.

BACKGROUND ART

A bone fracture is a break or crack in a bone, with complete or incomplete disruption of the continuity of a bone, epiphyseal plate or articular surface. A bone fracture is caused mostly by some type of trauma to a bone. This trauma might occur as a result of a motor vehicle accident, an accident in a workplace, physical abuse, repetitive stress such as exercise, heavy lifting, etc. Normal, everyday activities can cause bone fractures in people with diseases that weaken the bones, such as osteoporosis, bone cancer, or metabolic abnormalities. According to fracture line (line along epiphyseal ends generated upon fracture), bone fractures are classified into fissured fractures, greenstick fractures, transverse fractures, oblique fractures, spiral fractures, segmental fractures, comminuted fractures, avulsion fractures, compression fractures, depressed fractures, etc.

Generally, upon a bone fracture, injury of blood vessels occurs, incurring partial hemorrhage and blood clots. In addition, the bone matrix around a fracture region is broken down or ruptured, with the death of osteocytes. During a fracture healing process, hence, the blood clots and the injured osteocytes and bone matrix are removed by macrophages while osteoprogenitor cells of the perilsteum and endosteum around the fracture region actively proliferate to form cellular tissue around the fracture region and are then integrated with the fracture region. In the connective tissue of the fracture region, either a bone tissue arises by endochondral ossification from a small cartilage fragment or an immature bone is formed by intramembranous ossification. Accordingly, intramembranous ossification from mesenchymal tissue and endochondral ossification are observed concurrently in the connective tissue of a fracture region. The trabecula of the immature bone irregularly formed in this way temporarily connects ends of the fractured bone fragments, resulting in the formation of a bony callus. The woven bone of the bony callus formed in the fracture region is gradually resorbed as the healing process progresses, and undergoes rearrangement resulting in the development of lamellar bone.

As a rule, fracture healing is largely divided into three phases: inflammatory phase, bone reparative phase, and remodeling phase.

In the inflammatory phase, inflammatory responses occur since tissues around a fracture region are injured and hematoma fills the fracture gap.

In the bone reparative phase, the hematoma is removed from the fracture gap and substituted with granulation tissue while soft callus is formed. According to the osteogenesis mechanism, two processes proceed concurrently: endochondral ossification, in which the soft callus is remodeled into hard callus, and fibrous/intramembranous ossification, in which a new bone is formed by osteogenic cells.

In the remodeling phase, newly formed bone tissue is extended over a long period of time by the orchestrated action of osteoclastic bone resorption and osteoblastic bone formation, with the correction of bone distortions and the reinforcement of bone defects.

During the remodeling phase, patients with a bone fracture conduct their lives without great difficulty because the newly formed bone has become hard to some extent, but the nascent bone tissue in the reparative phase is not hard enough for patients to live their daily lives without difficulty. In addition, the reparative phase is long. Thus, it is clinically important for a fracture curative to have the function of shortening the reparative phase as well as regenerating a fractured bone into a complete bone by promoting the complex fracture healing process.

There are various promoters for fracture healing. Peptides having physiologically active functions, such as bone morphogenic proteins (BMPs) and transforming growth factors (TGFs), are found to be involved in the fracture healing process (Proc. Natl. Acad. Sci., USA, vol. 87, pp. 2220-2224 (1989)). Also, it has been studied that an increase in intracellular cyclic AMP level by use of a phosphodiesterase (PDE) inhibitor can lead to an increase in bone mass. For example, it is reported that mice, into which the general PDE inhibitor pentoxipylline or the selective PDE4 inhibitor rolipram had been subcutaneously injected every day, were observed to have the vertebrate and femur increased in bone mineral density, and showed hyperplasia of cortical bones (Bone, vol. 27., 6th edition, pp. 811-817 (2000)).

As mentioned above, attention has long been paid to osteogenesis and fracture healing, and extensive studies on fracture healing processes have been conducted from various points of view, including genetic factors, adolescent influence, hematopoietic effect, fixture effect, bone grafts, other healing promoting factors, etc. (Kawamura, M and Urist MR., Clin. Orthop., 236, 240-248, 1988).

Fracture healing requires a significant period of time and patients with osteoporosis tend to suffer more from bone fractures according to the increase of an aged population. Falling short of the expectation of usefulness in fracture healing, currently available therapeutic agents for the treatment of osteoporosis, such as calcium, estrogen, calcitonin, active vitamin D, bisphosphonate, etc., are found only to lower the risk of fracture by obstructing the decrease of bone density, but to have no function of joining fractured bones or generating bone tissues. The pathogenic mechanism of osteoporosis can be explained by a subtle bone matrix resulting from long maintenance of negative bone homeostasis due to genetic or constitutional predispositions, stagnant osteogenesis with normal bone resorption, and increased bone resorption with normal osteogenesis. The therapeutic agents for the treatment of osteoporosis are, therefore, ineffective for the treatment of bone fracture because the healing mechanism is quite different between fractures and osteoporosis.

Due to the mechanism difference between fractures and osteoporosis, anti-osteoporotic agents, having a function of inhibiting bone resorption, may obstruct bone formation, thereby actually retarding the fracture healing process. For example, incadronate disodium, a bisphosphonate agent, is reported to retard fracture healing in the femurs of rats administered therewith (Li C et al., J. Bone Miner Res. 2001 March; 16(3):429-36). Also there is a report describing that whereas the pretreatment with incardronate has no influence on fracture healing until 16 weeks after a bone fracture, continuous treatment with incardronate increases bony callus, but results in the retardation of the remodeling process (Li J et al., J. Bone Miner Res. 1999 June; 14(6):969-79).

bFGF, known as a bone formation biomarker highly associated with osteoporosis, is reported to have no relation to fracture healing (Xu et al., Chin. J. Traumatol. 6, 160~166, 2003).

For these reasons, currently available therapeutic agents for the treatment of osteoporosis are not adequate to apply to bone fractures. Therefore, there is an urgent need for a bone fracture curative that has great therapeutic effect on bone fractures, regardless of association with osteoporosis.

Leading to the present invention, intensive and thorough study on fracture healing, conducted by the present inventors, resulted in the finding that N-hydroxy-4-{5-[4-(5-isopropyl-2-methyl-1,3-thiazol-4-yl)phenoxy]pentoxy}-benzamidine and 4-{5-[4-(5-isopropyl-2-methyl-1,3-thiazol-4-yl)phenoxy]pentoxy}-benzamidine, developed as a medicament for the treatment of osteoporosis by the present inventors (Korean Pat. Unexamined Publication No. 10-2003-8654), can enhance the bone density and strength of the bony callus formed during a fracture healing process and promote endochondral ossification and intramembranous ossification in connective tissue, thereby exhibiting excellent healing effects on fractures, in spite of great differences between osteoporosis and fracture mechanisms.

DISCLOSURE OF THE INVENTION

Accordingly, the present invention has been made keeping in mind the above problems occurring in the prior art, and an object of the present invention is to provide a pharmaceutical composition for the treatment of bone fractures, comprising N-hydroxy-4-{5-[4-(5-isopropyl-2-methyl-1,3-thiazol-4-yl)phenoxy]pentoxy}-benzamidine, 4-{5-[4-(5-isopropyl-2-methyl-1,3-thiazol-4-yl)phenoxy]pentoxy}-benzamidine and pharmaceutically acceptable salts thereof.

Another object of the present invention is to provide a method of treating bone fractures using the composition.

BEST MODE FOR CARRYING OUT THE INVENTION

Figure 1:
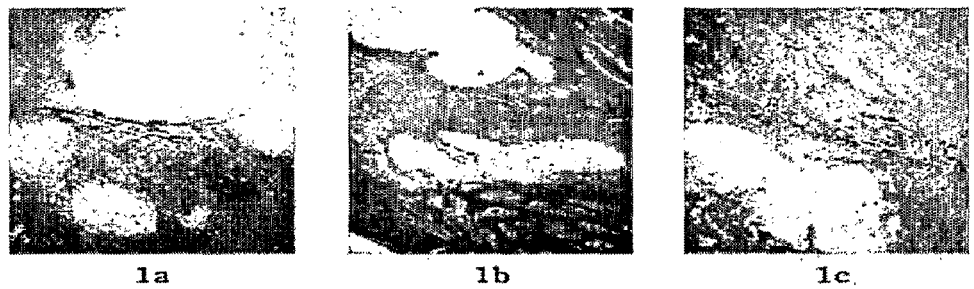
FIG. 1 an optical microphotograph showing sliced tissue specimens of the 8$^{th}$ rib extracted after fracture induction, stained with Masson's trichrome.
Figure 1:
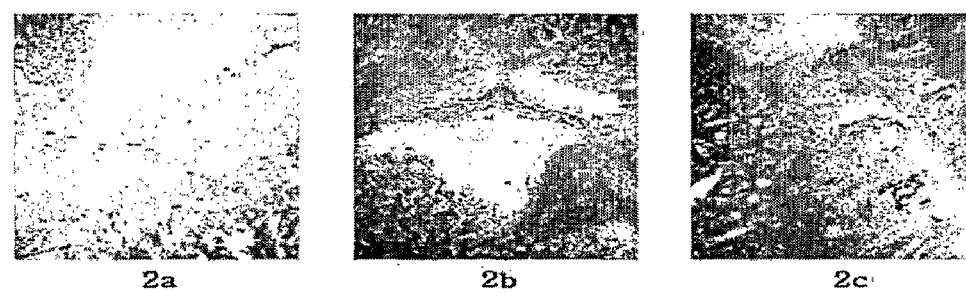
Figure 1:
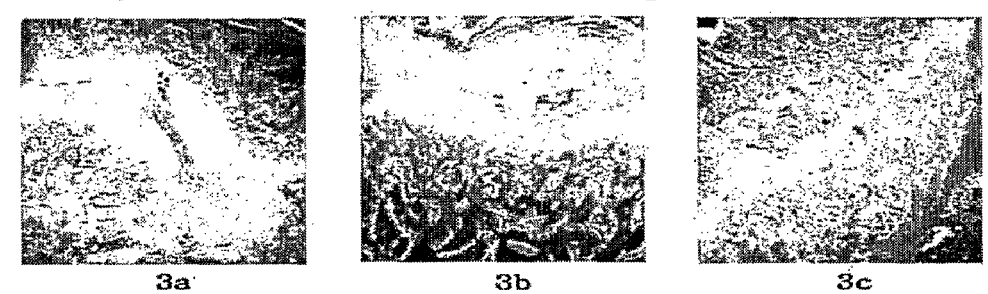
Figure 1:
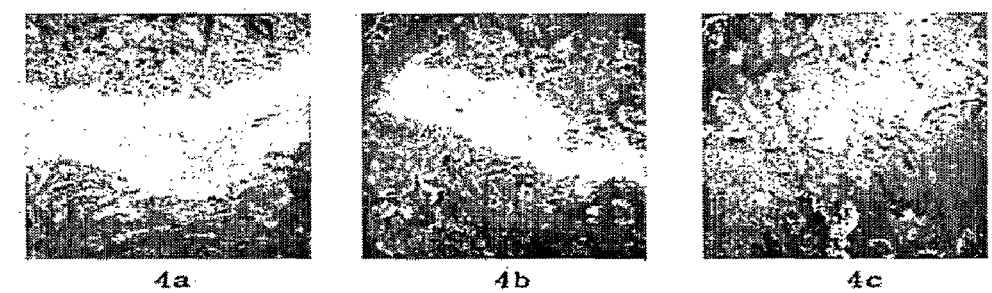

The present invention pertains to a pharmaceutical composition for the treatment of bone fractures, comprising a benzamidine compound represented by the following chemical formula 1 or a pharmaceutically acceptable salt thereof.

Chemical Formula 1

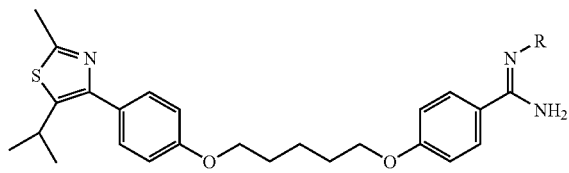

wherein, R is a hydrogen atom or a hydroxyl group.

The benzamidine compound of Chemical Formula 1 may be used in the form of pharmaceutically acceptable salts known in the art. Preferable are acid addition salts prepared with pharmaceutically acceptable free acids. Free acids suitable for use in the present invention may be inorganic acids or organic acids. Examples of the inorganic acids include hydrochloric acid, bromic acid, sulfuric acid, phosphoric acid, etc, and the organic acids may be exemplified by citric acid, acetic acid, lactic acid, tartaric acid, fumaric acid, formic acid, propionic acid, oxalic acid, trifluoroacetic acid, methane sulfonic acid, benzene sulfonic acid, maleic acid, benzoic acid, gluconic aicd, glycolic acid, succinic acid, 4-morpholine ethane sulfonic acid, camphorsulfonic acid, 4-nitrobenzene sulfonic acid, hydroxyl-O-sulfonic acid, 4-toluene sulfonic acid, galacturonic acid, embonic acid, glutamic acid and aspartic acid.

The benzamidine compound of Chemical Formula 1 may be prepared according to known processes (Lee, Sung-Eun, Synthesis and Biological Activity of Natural Products and Designed New Hybrid Compounds for the Treatment of LTB4 Related Disease, Busan National University, a thesis for a Ph. D degree, 1999. 8).

The term "bone fracture" as used herein means one of various physical injuries of a bone, based on a complete or incomplete disruption of the continuity of a bone, which are classified according to anatomical location (epiphyseal, metaphyseal, diaphyseal, intra-articular, proximal, midshaft, distal, etc.), degree of fracture (complete, incomplete), direction of fracture (transverse, oblique, spiral, longitudinal), presence of open wound (open, closed), number of fractures (simple, linear, segmental, comminuted, etc.), stability of fracture (stable, unstable), displacement of fracture, etc.

As compared to a non-treated group, a group treated with the benzamidine compound of Chemical Formula 1 according to the present invention was found to have the bony callus significantly decreased in volume in a dose-dependent pattern, but increased both in bone density and in bone strength, with significance, in a dose-dependent pattern ($p<0.01$ or $p<0.05$).

Treatment with the benzamidine compound of Chemical Formula 1 allowed the bony callus to significantly decrease in connective tissue and cartilage tissue while increasing the content of a bone tissue with significance ($p<0.01$ or $p<0.05$), compared to non-treatment. Both the decrease in connective tissue and cartilage tissue and the increase in bone tissue are dose-dependent.

In addition, the number of osteoclasts in a bony callus increased significantly upon treatment with the benzamidine compound of Chemical Formula 1, compared to non-treatment, in the early phase of the fracture healing process ($p<0.01$), and the increase pattern was dose-dependent.

In the late phase of the fracture healing process, a group treated with the benzamidine compound of Chemical Formula 1 had the bony callus decreased in the number of osteoclasts with significance, compared to a non-treated group ($p<0.01$), which indicates that ossification was already proceeding to some degree.

In summary, the benzamidine compound of Chemical Formula 1 is an effective curative for bone fractures, with functions of promoting the loss and ossification of the bony callus formed during the fracture healing process. In more detail, the benzamidine compound of the present invention increases cellular components of bony callus in the early phase of bone fracture healing process and promotes endochondral ossification and intramembranous ossification in the late phase in bone fracture healing process.

The composition of the present invention may further comprise at least one effective ingredients which are equivalent or similar function to that of the benzamidine compound of Chemical Formula 1 or its pharmaceutically acceptable salt.

The composition of the present invention may further comprise one or more pharmaceutically acceptable carriers. A proper carrier may be selected from a group consisting of saline, sterilized water, Ringer's solution, buffered saline, a dextrose solution, a maltodextrin solution, glycerol, ethanol, and combinations thereof, and may be, if necessary, further supplemented with other typical additives such as an antioxidant, a buffer, a static agent, etc. In combination with a diluent, a dispersant, a surfactant, a binder, and a lubricant, the composition of the present invention may also be formulated into injectable dosage forms, such as aqueous solutions, suspensions, emulsions, etc., pills, capsules, granules, and tablets. Moreover, depending on the kind of ingredient or disease, the formulation may be conducted using methods known in the art or disclosed in Remington's Pharmaceutical Science ((latest version), Mack Publishing Company, Easton Pa.).

According to purposes, the composition of the present invention may be administered orally or parenterally (e.g., intravenously, subcutaneously, intraabdominally, or topically). The dosage amount of the composition of the present invention varies depending on body weight, age, gender, health state, diet, administration time period, administration route, excretion rate, disease severity, etc. When all of these factors are taken into account, the benzamidine compound of Chemical Formula 1 is administered once or many times at a dose of approximately 10 to 1,000 mg/kg a day, and preferably at a dose of approximately 50 to 500 mg/kg a day.

For the prevention and treatment of physical injury of bone comprising fracture, the composition of the present invention can be used alone or in combination with surgery, hormone therapy, chemical therapy, and/or a biological response controller.

A better understanding of the present invention may be obtained through the following examples which are set forth to illustrate, but are not to be construed as the limit of the present invention.

EXAMPLE

Effect of Promoting Fracture Healing in Rib Fracture-Induced Rat Model

The benzamidine compound of Chemical Formula 1 was assayed for therapeutic effect on bone fracture in rat models subjected to rib fracture. Starting from 2 days after the induction of rib fracture, the administration of the benzamidine compound was continued for one, two, three and four weeks. Changes in (body weight, body weight gain, volume of bony callus, bone density, bone strength, and bone histopathology were observed.

1. Experimental Animals and Breeding Management

A total of 80 S.D. rats (10-week-old, BioGenomics, Korea) was adapted to a laboratory environment for 12 days before being used in experiments. While being housed at a density of two or three to a plastic cage, the experimental animals were kept in a breeding room under controlled temperature (20 to 25° C.) and humidity (30 to 35%). Under light-dark cycles of 12 hours, the rats were allowed to have free access to feedstuff and tap water.

2. Preparation and Administration of Sample 10 mg and 50 mg of N-hydroxy-4-{5-[4-(5-isopropyl-2-methyl-1,3-thiazol-4-yl)phenoxy]pentoxy}benzamidine were completely dissolved in 5 ml of sterilized distilled water. The benzamidine compound in the solutions was orally administered at doses of 10 mg and 50 mg per kg of body weight once a day for one, two, three and four weeks from day 2 of the surgery.

3. Induction of Rib Facture

All the experimental animals were anesthetized with ketamine hydrochloride and xylazine hydrochloride and underwent an operation for inducing a fracture on the 8th and the 9th rib. In this regard, the ribs were transversely cut with operation scissors. After the fracture induction, the fractured ribs were assembled to be aligned with each other and the wound cavity was closed through skin suture.

4. Change in Body Weight and Weight Gain

All the experimental animals were measured for body weight one day before the operation, the day of the operation, the day of administration, and 7, 14, 21 and 28 days after administration. In order to reduce the difference among individuals due to feedstuff intake, all experimental animals were starved for 18 hours or more on the day of the measurement. Also, to minimize the difference of change in body weight of individual animals, body weight gain during time periods from the day of the operation to 7, 14, 21 and 28 days after the administration were calculated.

The results are given in Table 1, below.

TABLE 1

| Experimental Groups | | Changes in Body Weight Gain (g) days after administration | | | |
|---|---|---|---|---|---|
| | | 7 days | 14 days | 21 days | 28 days |
| Control | | 18.80 ± 12.07 | 40.20 ± 25.07 | 63.40 ± 15.68 | 71.60 ± 15.82 |
| Cpd. Of Chemical Formula 1 | 10 (mg/kg) | 16.00 ± 13.55 | 44.40 ± 14.54 | 46.40 ± 22.39 | 61.20 ± 22.81 |
| | 50 (mg/kg) | 14.80 ± 08.81 | 36.82 ± 29.52 | 68.60 ± 16.65 | 84.40 ± 23.37 |

As seen in Table 1, no significant changes in body weight gain were observed over all experimental periods, indicating that there were almost no errors attributable to the administration of experimental substances or individual differences between experimental animals.

5. Volume of Bony Callus

On the sacrificial day, the bony callus formed around the fractured 8th and 9th ribs was separated from adjacent tissues and taken out of all experimental animals. The enucleated bony calluses were measured for long and short diameters in millimeters. The volume of the bony callus was calculated from the measurements using the following mathematic formula 1.

$$\text{Volume of Bony callus} = \frac{1}{2} \times (a \times b^2) \quad \text{Formula 1}$$

a: long diameter of bony callus, b: short diameter of bony callus.

The results are given in Table 2, below.

TABLE 2

| Experimental | | Changes in Bony Callus Volume ($mm^3$) Days After Administration | | | |
|---|---|---|---|---|---|
| Groups | | 7 days | 14 days | 21 days | 28 days |
| Control | | 35.35 ± 7.96 | 19.09 ± 3.11 | 11.69 ± 4.15 | 9.25 ± 3.00 |
| Cpd. of | 10 (mg/kg) | 12.84 ± 4.42* | 5.47 ± 1.81* | 4.73 ± 2.13* | 3.96 ± 2.41* |
| Chemical Formula 1 | 50 (mg/kg) | 8.62 ± 3.43* | 4.36 ± 1.44* | 3.84 ± 1.86* | 3.37 ± 0.79* |

*significance compared to control ($p < 0.01$)

As is apparent from Table 2, the volume of bony callus according to fracture healing was significantly decreased in the benzamidine compound-administered group, compared to the non-treated control group ($p<0.01$), in a dose-dependent pattern.

Thus, the benzamidine compound of Chemical Formula 1 is found to promote the loss of the bony callus formed during the fracture healing process.

6. Histopathological observation

The 8th rib enucleated after the fracture induction was fixed in 10% neutral formalin, followed by decalcification by changing a decalcification solution (2.24% formic acid, 0.5N sodium hydroxide) with fresh solution once a day for five days. After completion of the decalcification, the rib was embedded in paraffin. The paraffin-embedded tissue was sliced at a thickness of 3 to 4 μm, stained with hematoxylin-eosin or Masson's trichrome and observed through an optical microscope.

The results are given in FIG. 1.

The benzamidine compound-administered group, as shown in FIG. 1, was found to have increased bone tissue in bony callus in all administration time periods, as opposed to the none-treated group, and the increased behavior of the bone tissue was observed to be dose-dependent.

Hence, the benzamidine compound of Chemical Formula 1 can promote bone formation in the bony callus formed upon fracture.

From the rib tissue specimen prepared above, the amounts of the connective tissue, cartilage and bone tissue in the bony callus were examined using an Analysis Image processing system (SIS Germany) and are represented as percentages in Tables 3 to 5, below.

Furthermore, the number of osteoclasts in the bony callus, particularly, within an area of $(200\ \mu m)^2$ on the fracture surface at which endochondral ossification commenced, was measured using an Analysis Image processing system (SIS Germany).

The results are given in Table 6, below.

TABLE 3

| Experimental | | Changes in Content of Connective Tissue of Bony Callus Days after Administration (% relative to total bony callus) | | | |
|---|---|---|---|---|---|
| Groups | | 7 days | 14 days | 21 days | 28 days |
| Control | | 51.34 ± 11.55 | 19.43 ± 2.01 | 15.10 ± 2.96 | 7.14 ± 2.73 |
| Cpd. Of | 10 (mg/kg) | 33.19 ± 3.06 | 6.28 ± 0.72* | 5.55 ± 1.42* | 3.20 ± 0.89* |
| Chemical Formula 1 | 50 (mg/kg) | 29.51 ± 5.70** | 6.06 ± 0.44* | 3.58 ± 0.62* | 2.59 ± 0.52* |

*significance compared to control($p < 0.01$),
**significance compared to control($p < 0.05$)

As seen in Table 3, the benzamidine compound-administered group decreased dose-dependently in the content of connective tissue within the bony callus tissue, compared to the non-treated group, with significance ($p<0.01$ or $p<0.05$).

As a result, the benzamidine compound of Chemical Formula 1 is identified to promote the substitution of bone tissue for the connective tissue within the bony callus formed upon fracture, that is, ossification.

TABLE 4

| Experimental | | Changes in Content of Cartilage Tissue in Bony Callus Days After Administration (% relative to total bony callus) | | | |
|---|---|---|---|---|---|
| Groups | | 7 days | 14 days | 21 days | 28 days |
| Control | | 43.28 ± 4.66 | 39.49 ± 2.79 | 24.93 ± 4.13 | 17.78 ± 2.30 |
| Cpd. Of | 10 (mg/kg) | 24.79 ± 5.43* | 23.77 ± 3.44* | 18.51 ± 2.29* | 6.59 ± 2.02* |
| Chemical Formula 1 | 50 (mg/kg) | 22.42 ± 5.45* | 20.09 ± 6.38* | 11.49 ± 2.31* | 5.37 ± 1.38* |

*significance compared to control($p < 0.01$)

The cartilage tissue within the bony callus tissue, as is apparent from Table 4, was significantly decreased in the benzamidine compound-administered group, as compared to the non-treated group, in a dose-dependent pattern (p<0.01).

Accordingly, the benzamidine compound of Chemical Formula 1 is identified to promote the substitution of bone tissue for the cartilage tissue within the bony callus formed upon fracture, that is, endochondral ossification.

TABLE 5

| Experimental Groups | | Changes in Content of Bone Tissue in Bony Callus Days After Administration (% relative to total bony callus) | | | |
|---|---|---|---|---|---|
| | | 7 days | 14 days | 21 days | 28 days |
| Control | | 1.92 ± 0.70 | 38.21 ± 4.92 | 54.49 ± 6.04 | 66.88 ± 5.68 |
| Cpd. Of Chemical Formula 1 | 10 (mg/kg) | 37.95 ± 6.44* | 54.31 ± 9.50** | 66.71 ± 5.41** | 83.30 ± 4.43* |
| | 50 (mg/kg) | 39.24 ± 14.12* | 55.94 ± 8.38* | 74.07 ± 8.43* | 87.27 ± 8.97** |

*significance compared to control($p < 0.01$),
**significance compared to control($p < 0.05$)

As seen in Table 5, the bone tissue within the bony callus was significantly increased in the benzamidine compound-administered group, compared to the non-treated group ($p<0.01$ or $p<0.05$) in a dose-dependent pattern.

Thus, the benzamidine compound of Chemical Formula 1 is identified to promote the ossification of the bony callus formed during the fracture healing process.

TABLE 6

| Experimental Groups | | Changes in Population of Osteoclasts within Bony Callus Days After Administration (Counts present within $(200 \mu m)^2$ of bony callus) | | | |
|---|---|---|---|---|---|
| | | 7 days | 14 days | 21 days | 28 days |
| Control | | 15.80 ± 1.92 | 21.80 ± 3.35 | 56.80 ± 3.03 | 41.60 ± 11.46 |
| Cpd. Of Chemical Formula 1 | 10 (mg/kg) | 43.80 ± 3.83* | 50.60 ± 2.70* | 31.00 ± 6.67* | 21.60 ± 3.58* |
| | 50 (mg/kg) | 42.60 ± 4.62* | 53.60 ± 2.41* | 22.20 ± 3.03* | 17.60 ± 2.97* |

*significance compared to control($p < 0.01$)

In the early phase of the facture healing process, as seen in Table 6, the number of osteoclasts in the bony callus was increased in the benzamidine compound-administered group, compared to the non-treated group, with significance (p<0.01), and the number of osteoclasts was found to increase as the dosage increased. Thus, the administration of the benzamidine compound of Chemical Formula 1 leads to a dose-dependent increase in cellular components within bony callus in the early phase of the fracture healing process.

In the late phase of the fracture healing process, a group treated with the benzamidine compound of Chemical Formula 1 had the bony callus decreased in the number of osteoclasts with significance, compared to a non-treated group (p<0.01), which indicates that ossification was already proceeding to some degree.

In conclusion, the benzamidine compound of Chemical Formula 1 is very useful as a curative for bone fractures, with the function of promoting the ossification of the bony callus formed upon fracture.

7. Measurement of Bone Density of Bony Callus

The 9th rib enucleated after the fracture induction was measured for the bone density around the bony callus using dual-energy x-ray absorptiometry (DEXA, PXImus; Lunar Medison, Wis.) and the bone density is calculated in $mg/cm^2$ in Table 7.

TABLE 7

| Experimental Groups | | Changes in Bone Density of Bony Callus Days After Administration ($mg/cm^2$) | | | |
|---|---|---|---|---|---|
| | | 7 days | 14 days | 21 days | 28 days |
| Control | | 0.12 ± 0.04 | 0.22 ± 0.03 | 0.28 ± 0.08 | 0.39 ± 0.07 |
| Cpd. Of Chemical Formula 1 | 10 (mg/kg) | 0.24 ± 0.04* | 0.32 ± 0.04* | 0.39 ± 0.04** | 0.55 ± 0.06** |
| | 50 (mg/kg) | 0.24 ± 0.03* | 0.32 ± 0.04* | 0.44 ± 0.07** | 0.57 ± 0.04** |

*significance compared to control($p < 0.01$),
**significance compared to control($p < 0.05$)

The benzamidine compound-administered group, as is apparent from the data of Table 7, increased in the bone density of the bony callus, compared to the non-treated control, with significance (p<0.01 or p<0.05), and the bone density increased as the dose increased.

Therefore, the benzamidine compound of Chemical Formula 1 is identified to increase a bone density of the bony callus formed upon fracture.

8. Measurement of Bone Strength of Bony Callus

The bone strength around the fracture face at which a bony callus was formed in the 9th rib enucleated after the fracture induction was determined from three point bending tests using an Instron material testing system (Instron 6022; Instron, USA; speed 20 mm/min).

The results are given in Table 8, below.

TABLE 8

| Experimental | Changes in bone strength of bony callus Days After Administration (Nos. of Impact applied) | | | |
|---|---|---|---|---|
| Groups | 7 days | 14 days | 21 days | 28 days |
| Control | 1.24 ± 0.28 | 1.53 ± 0.51 | 2.06 ± 0.18 | 2.38 ± 0.22 |
| Cpd. Of Chemical Formula 1   10 (mg/kg) | 2.15 ± 0.42** | 2.57 ± 0.65* | 3.10 ± 0.40* | 3.26 ± 0.43** |
| Cpd. Of Chemical Formula 1   50 (mg/kg) | 2.35 ± 0.47** | 2.84 ± 0.34* | 3.23 ± 0.35* | 3.35 ± 0.38** |

*significance compared to control (p < 0.01),
**significance compared to control (p < 0.05)

As seen in Table 8, the benzamidine compound-administered group increased in the bone strength, compared to the non-treated group, with significance (p<0.01 or p<0.05) in a dose-dependent pattern.

As a consequence, the benzamidine compound of Chemical Formula 1 is identified to increase the bone strength in the bony callus formed upon fracture.

9. Statistics

All numerals are represented as mean ±standard deviation, and statistical significance of the differences relative to the control was analyzed using Mann-Whitney U-Wilcoxon Rank Sum test with the aid of SPSS (Release 6.1.3., SPSS Inc., USA).

Likewise, methane sulfonic acid salts and hydrochloric acid salts of N-hydroxy-4-{5-[4-(5-isopropyl-2-methyl-1,3-thiazol-4-yl)phenoxy]pentoxy}benzamidine, and 4-{5-[4-(5-isopropyl-2-methyl-1,3-thiazol-4-yl)phenoxy]pentoxy}benzamidine and its methane sulfonic acid salts and hydrochloric acid salts were found to exhibit the same healing effects as above.

Preparation Example

| 1. Preparation of powder | |
|---|---|
| Benzamidine compound of Chemical Formula 1 | 2 g |
| Lactose | 0.5 g |
| Mannitol | 0.5 g |

The ingredients were mixed and filled in an airtight sac to prepare a powder agent.

| 2. Preparation of tablet | |
|---|---|
| Benzamidine compound of Chemical Formula 1 | 100 mg |
| Corn Starch | 50 mg |
| Microcrystalline Cellulose | 50 mg |
| Lactose | 100 mg |
| Povidone | 15 mg |
| Magnesium Stearate | 2 mg |

A mixture of the ingredients was prepared into a tablet using a general tabletting method.

| 3. Preparation of capsule | |
|---|---|
| Benzamidine compound of Chemical Formula 1 | 100 mg |
| Corn Starch | 50 mg |
| Microcrystalline Cellulose | 50 mg |
| Lactose | 100 mg |
| Povidone | 15 mg |
| Magnesium Stearate | 2 mg |

A mixture of the ingredients was filled into a gelatin capsule according to a typical procedure, so as to give a capsule agent.

| 4. Preparation of soft capsule | |
|---|---|
| Benzamidine compound of Chemical Formula 1 | 100 mg |
| Soybean Oil | 400 mg |
| Lecithin | 20 mg |
| Gelatin | 200 mg |

A soft capsule was prepared from the mixture of the ingredients, according to a typical procedured.

| 5. Preparation of injection | |
|---|---|
| Benzamidine compound of Chemical Formula 1 | 10 µg/ml |
| Diluted Hydrochloric acid BP | to pH 3.5 |
| Injectable Sodium chloride BP | 1 ml at most |

A solution of the benzamidine compound of Chemical Formula 1 in a proper volume of injectable sodium chloride BP was adjusted to pH 3.5 with diluted hydrochloric acid BP and its volume was adjusted with injectable sodium chloride BP. After being sufficiently mixed, the solution was filled in a 5 ml type I ampul made from transparent glass, which was then molten so that the solution was packaged under the upper grid of air. An injection was obtained by autoclaving at 120° C. for 15 min or longer.

INDUSTRIAL APPLICABILITY

The composition of the present invention can significantly reduce the volume of bony callus, increase bony density and strength of bony callus, and decrease the contents of connective tissue and cartilage tissue in bony callus, and thus promote loss and ossification of the bony callus formed during the fracture healing process. Therefore, the composition of the present invention is useful for the treatment of bone fracture.

The invention claimed is:

1. A method of treating bone fracture, the method comprising:
   (a) identifying a patient with a bone fracture resulting from physical trauma; and
   (b) administering to the patient a benzamidine compound represented by the following chemical formula 1 or its pharmaceutically acceptable salt Chemical Formula 1 wherein R is hydrogen or hydroxyl.

2. The method of treating bone fracture according to claim 1, wherein administration of said compound results in an increase in bone density of a bony callus of said patient.

3. The method of treating bone fracture according to claim 1, wherein administration of said compound results in an increase in the strength of a bony callus of said patient.

4. The method of treating bone fracture according to claim 1, wherein administration of said compound results in promotion of ossification of connective tissue of a bony callus of said patient.

5. The method according to claim 4, wherein the ossification is endochondral ossification.

6. The method according to claim 4, wherein the ossification is intramembraneous ossification.

7. The method according to claim 4, wherein the ossification is endochondral ossification and intramembraneous ossification.

8. A method of increasing the number of osteoclasts in a bony callus of a fractured bone of a patient during the early stage of recovery from a bone fracture, the method comprising administering to the patient at the early stage of recovery from a bone fracture a benzamidine compound represented by the following chemical formula 1 or its pharmaceutically acceptable salt:

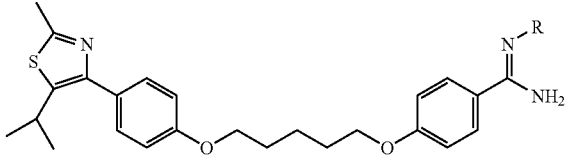

Chemical Formula 1 wherein R is hydrogen or hydroxyl.

9. The method of treating bone fracture according to claim 1, wherein administration of said compound results in a decrease in the number of osteoclasts in a bony callus of said patient during the late stage of recovery from a bone fracture.

10. The method of treating bone fracture according to claim 1, further comprising the step of treating said patient with one or more additional therapies selected from the group consisting of surgery, hormone therapy, chemical therapy, and a biological response controller.

11. The method of treating bone fracture according to claim 1, wherein the pharmaceutically acceptable salt is an acid addition salt.

12. The method of treating bone fracture according to claim 1, wherein the pharmaceutically acceptable salt is a methane sulfonic acid salt or hydrochloric acid salt.

* * * * *